United States Patent
Beltre et al.

(10) Patent No.: US 11,189,365 B2
(45) Date of Patent: *Nov. 30, 2021

(54) MONITORING CLINICAL RESEARCH PERFORMANCE

(71) Applicant: International Business Machines Corporation, Armonk, NY (US)

(72) Inventors: Cerdi Beltre, Cary, NC (US); Leslie B. Montejano, North Adams, MA (US); Prasanna Rao, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 212 days.

This patent is subject to a terminal disclaimer.

(21) Appl. No.: 16/449,683

(22) Filed: Jun. 24, 2019

(65) Prior Publication Data

US 2019/0311788 A1 Oct. 10, 2019

Related U.S. Application Data

(63) Continuation of application No. 15/938,611, filed on Mar. 28, 2018.

(51) Int. Cl.
*G16H 10/20* (2018.01)
*G16H 50/30* (2018.01)
(Continued)

(52) U.S. Cl.
CPC .............. *G16H 10/20* (2018.01); *G06N 20/00* (2019.01); *G06Q 10/06398* (2013.01); *G16H 50/30* (2018.01)

(58) Field of Classification Search
CPC .................................................... G16H 40/20
See application file for complete search history.

(56) References Cited

U.S. PATENT DOCUMENTS

2005/0182657 A1 8/2005 Abraham-Fuchs et al.
2006/0248031 A1 11/2006 Kates et al.
(Continued)

FOREIGN PATENT DOCUMENTS

WO 2006138116 A2 12/2006
WO 2008127733 A1 10/2008
(Continued)

OTHER PUBLICATIONS

Ghelli et al., On the Use of the Extreme Dependency Score to Investigate the Performance of an NWP Model for Rare Events, Meteorological Applications, Dec. 2009, pp. 537-544.
(Continued)

*Primary Examiner* — Sheetal R Paulson
(74) *Attorney, Agent, or Firm* — Will Stock; Edell, Shapiro & Finnan, LLC

(57) ABSTRACT

A computer-implemented method, system, and computer program product monitors clinical research performance. One or more metrics of clinical research performance for investigator/provider/research sites across research studies are collected. The metrics include performance area, characteristic of the performance area with one or more attributes, point values for each attribute, and weight value for the characteristic. A performance score is produced for each of the entities based on the one or more metrics. A machine learning model is trained to determine performance scores based on the produced performance score for each of the entities. A request for entities is processed by applying performance scores from the machine learning model and appropriate corresponding data to a predictive model to determine resulting performance scores, rank and/or match for each of the one or more entities for a given protocol and/or assessment trigger. Actions are performed based on the resulting performance scores, rank and/or match.

5 Claims, 5 Drawing Sheets

(51) Int. Cl.
*G06Q 10/06* (2012.01)
*G06N 20/00* (2019.01)

(56) References Cited

U.S. PATENT DOCUMENTS

| | | |
|---|---|---|
| 2015/0220868 A1 | 8/2015 | Elashoff |
| 2015/0242793 A1 | 8/2015 | Williams et al. |
| 2016/0092641 A1 | 3/2016 | Delaney et al. |
| 2016/0092658 A1 | 3/2016 | Leenaerts |
| 2016/0147953 A1 | 5/2016 | Memon et al. |
| 2016/0180275 A1 | 6/2016 | Piazza et al. |
| 2019/0304575 A1 | 10/2019 | Beltre et al. |

FOREIGN PATENT DOCUMENTS

| | | |
|---|---|---|
| WO | 2016099576 A1 | 6/2016 |
| WO | 2018208936 A1 | 11/2018 |

OTHER PUBLICATIONS

List of IBM Patents or Patent Applications Treated as Related, filed Jun. 24, 2019.

MONITORING CLINICAL RESEARCH PERFORMANCE

BACKGROUND

1. Technical Field

Present invention embodiments generally relate to monitoring clinical research performance and optimizing the use of data in assessing performance of research sites and investigators. More particularly, the present invention embodiments relate to collecting and evaluating metrics of clinical research performance for individual entities (e.g., investigators, providers, research sites, studies, etc.) across various aspects of clinical research studies.

2. Discussion of the Related Art

One of the most significant challenges for the clinical research industry is to determine the most suitable and efficient investigators or research sites to execute clinical research studies. Different entities within the industry, such as study sponsors, foundations, private donors, academic medical centers, government sponsors, etc., are interested in selecting investigators and appropriate research sites that will deliver good performance according to the precise needs of their clinical research studies. However, the metrics and the site optimization strategy information relating to an investigator's clinical research performance history, as well as the relevant study patient population information, are typically stored in multiple data repositories. Accessing and collecting information from multiple data repositories can not only be time consuming and labor intensive, but it can result in incomplete information being gathered.

SUMMARY

According to one embodiment of the present invention, the clinical research performance of one or more entities are monitored by collecting one or more metrics of clinical research performance for the one or more entities across research studies. Each metric includes a performance area, a characteristic of the performance area with one or more attributes, point values for each attribute, and a weight value for the characteristic. A performance score is produced for each of the entities based on the one or more metrics (e.g., investigator performance score, provider score, research sites performance score). A machine learning model is trained to determine performance scores (and/or rank) based on the produced performance score for each of the entities. A request for entities is processed by applying the performance scores from the machine learning model and appropriate corresponding data to a predictive model to determine resulting performance scores (and/or rank) for each of the one or more entities. Various actions are performed based on the resulting performance scores (rank and/or match) of the one or more entities.

Other aspects of the embodiments of the present invention presented herein will be apparent from the following detailed description taken in connection with the accompanying drawings.

BRIEF DESCRIPTION OF THE DRAWINGS

Embodiments of the present invention are described herein in conjunction with the accompanying drawings, in which.

DETAILED DESCRIPTION

Figure 1:
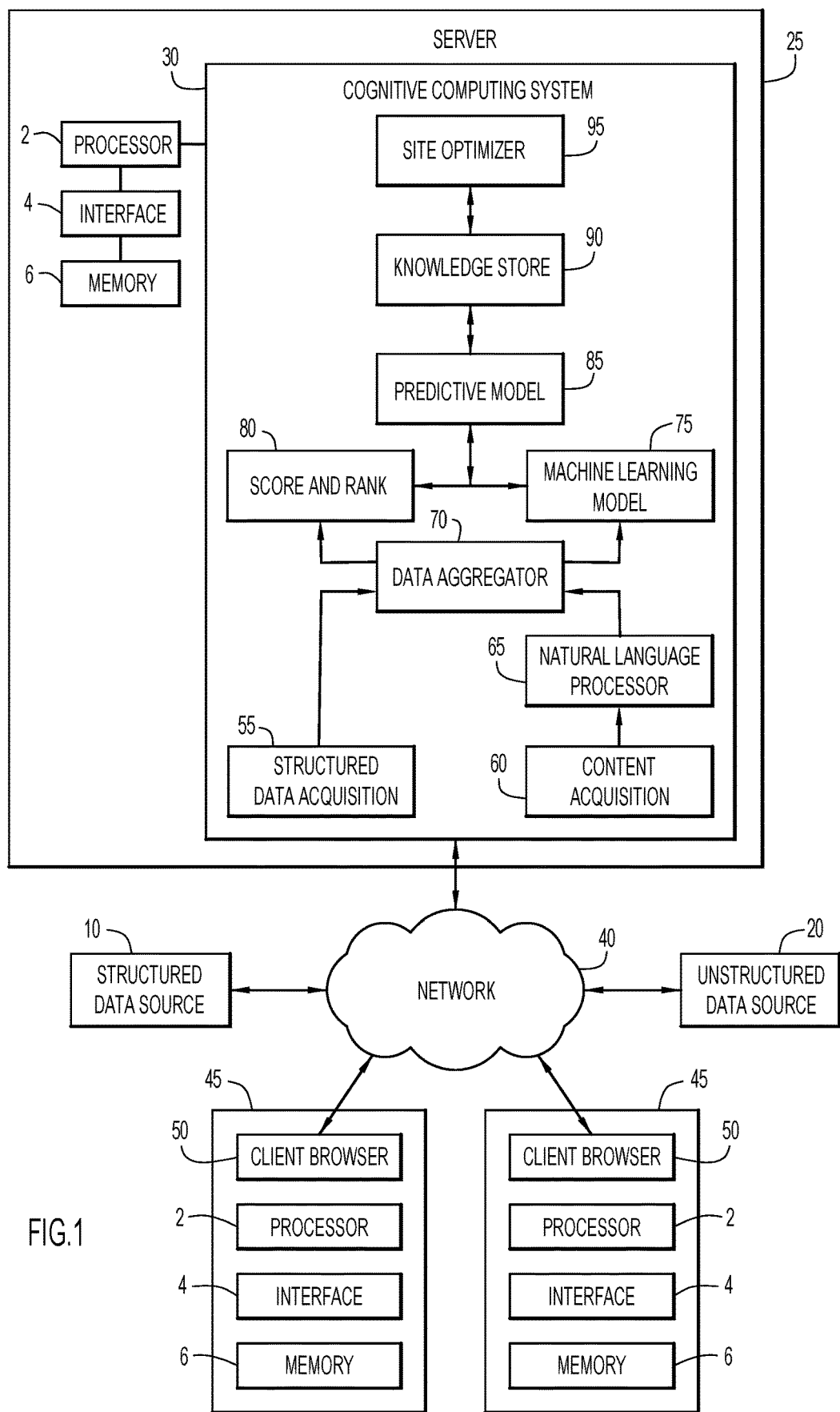
FIG. 1 depicts a schematic block diagram illustrating an example computing environment in which the present general inventive concept can be embodied.

The present inventive concept is best described through certain embodiments thereof, which are described in detail herein with reference to the accompanying drawings, wherein like reference numerals refer to like features throughout. It is to be understood that the term invention, when used herein, is intended to connote the inventive concept underlying the embodiments described below and not merely the embodiments themselves. It is to be understood further that the general inventive concept is not limited to the illustrative embodiments described below and the following descriptions should be read in such light.

Additionally, the word exemplary is used herein to mean, "serving as an example, instance or illustration." Any embodiment of construction, process, design, technique, etc., designated herein as exemplary is not necessarily to be construed as preferred or advantageous over other such embodiments.

With respect to the description of embodiments:

Clinical research generally refers to an investigation in which one or more human subjects are prospectively assigned to one or more interventions (which may include placebo or other control) to evaluate the effects of those interventions on health-related biomedical or behavioral outcomes; also referred to as a research study, clinical investigation, clinical trial, study, and human subject research.

An investigator generally relates to a person responsible for the conduct of a research study at a research site; also known as a principal investigator (PI).

A provider generally relates to a health care professional who helps in identifying, preventing or treating illness/disability.

A site generally relates to a facility/entity/business where a research study can be conducted, e.g., academic medical center, hospital or research facility; also known as a research site. For providers in private practice, the site typically would be Dr. X's practice (Dr. X could be the sole employee of such site). However, for clinicians with privileges at a facility/entity/business or employed by a facility/entity/business, the site would be the facility, entity or business.

Moreover, a single clinician could be associated with one or more sites, and the one or more sites with which a clinician is associated may change over time.

An investigator performance score generally relates to an individual research investigator score based on a model from metrics collected from research studies. It is conceived as a predictor of success in a future study based on available data on general qualifications and past behaviors (including study performance and other domains). The metrics compare individual investigator performance across different domains within each multi-site study. This provides a comparison of investigators across peers conducting the same research study. The score can be used for process improvement, benchmarking, and an investigator's own marketing. The investigator can receive offers from businesses that provide resources/solutions to improve their ability to follow through on clinical research commitments in the future.

Investigator Background and Expertise generally relates to metrics derived from a process that associates publications, affiliations, etc. with individual investigators or providers so this information can be used as part of the score or rank. The data from the research site performance score is also used here.

Investigator and site rank generally refers to an investigator and site ranking using a site performance score in addition to the investigator performance score and key opinion leader information, as selected. It uses the same data from the first two, however, the user now has the option for assessment triggers (i.e. patient volume, compliance history, ethical conduct, study history length, etc.) on this data, as will be discussed in detail below.

The site performance score is a model based on metrics from different domains. The rank pulls from multiple sources of data to rank sites to determine the best sites for the particular user-defined study indication. This capability has predictive capabilities on who might be the best site/investigator and why. It provides a manner for the user to give real time feedback on the ranked sites. The user's feedback will be recorded, stored and used to document human decisions in the process. In this capability, users can opt to consider a site's patient population volumes, competing ongoing studies, resources, study coordinator staffing, institutional support, etc.

Protocol to site and investigator match generally relates information based on the eligibility criteria from a protocol. It may be based on study operations and what is available at sites (e.g., does the site have a −70 degree freezer?). With this information, one may add priority triggers and patient population volumes, as well as predict enrollment, start-up, and conflicts.

Present invention embodiments provide a web-based computer-implemented system running software applications, such as a Software as a Service (SaaS) application, which permits a user to manage various aspects of their clinical research studies. The system includes a hosted web application for a client-server architecture that permits users to add data from various data sources to configure and manage their clinical research projects. In addition, the system provides users with a universal or standard method for scoring an investigator, provider, and a research site's performance in clinical research that can be adopted across the industry. Cognitive computing optimizes the performance scores to a higher degree of precision with iterative machine learning capabilities that accommodates a user/machine interaction for developing site optimization strategy for a given research study.

Present invention embodiments further provide an easily understood performance score and a ranked match for a given protocol parameter that will represent an investigator's ability to follow-through on their research commitments such that study sponsors, foundations, private donors, academic medical centers, government sponsors, etc., can quickly identify appropriate performance history, reduce investment risk, and increase chances for meeting enrollment targets and contract/agreement expectations using the system recommended site optimization strategy.

In accordance with aspects of certain embodiments presented herein, the approach to determine the most suitable and efficient candidates to participate in clinical research trials includes gathering and associating data around investigators, providers, and research sites to predict which investigators or providers would perform best for a particular research study and, where possible, cognitively match protocol eligibility criteria to particular sites based on site characteristics including their patient population. Further, the data could provide performance insights about sponsors and contract research organizations (CRO), as well as service/technology providers, using past study performance data.

In accordance with aspects of other embodiments presented herein, metrics of clinical research performance for individual investigators, providers, and research sites are associated with patient population data (e.g., number of patients meeting protocol inclusion and exclusion criteria), clinical research experience, and other sources of data to produce study-specific protocol eligibility-based performance score, rank, and match of investigators, providers, and/or research sites for a particular clinical research study. Using cognitive technology, various structured and unstructured data can be analyzed to derive the score, rank, and match, and to predict the best performing investigators and sites. Further, the analyzed structured and unstructured data can be used to provide investigators/research sites with performance/resource information to drive behavior change, as needed.

In accordance with aspects of further embodiments presented herein, study-specific protocol eligibility criteria can be submitted into a platform and parsed to determine the best matched investigators, providers, and/or research sites. Hierarchical views of investigator, provider, and/or research site scoring graphs are created by a computing system. Predictive analytical models are built on top of the scoring graphs to sort and rank the investigators, providers and/or research sites for the particular study. The rankings are presented to the user in the context of a proposed site optimization strategy/plan. Real time user feedback regarding the proposed plan is incorporated through machine learning models to optimize the final choice of investigators, providers, and/or research sites to meet the patient recruitment goal for a given study.

An exemplary related product to certain embodiments of the performance score aspect of the present invention is the U.S. credit rating score, e.g., Equifax's credit score range, which uses a three-digit number, typically between 300 and 850, designed to represent a person's credit risk, or likelihood to pay their bills on time. The credit score is calculated based on a method using content contained within the person's consumer file.

Whereas the exemplary U.S. credit rating score discussed above relates to a person's ability to follow-through on financial commitments, the example performance score generated as part of the present invention is designed to be a universal or standard performance score which would objectively and verifiably indicate to the clinical research industry an investigator's ability to follow-through on his/her research study commitments. This score is the basis for the ranking of the investigators that is done per individual study through a novel method of predictive analytics and user/machine interaction. The optimization goal is to discern the best possible investigators and the sites that will yield the appropriate patients for a given study using the site optimizer module.

An example environment for use with present invention embodiments is illustrated in FIG. 1. Specifically, the environment includes a computer server system 25 employing a cognitive computing system 30; client systems 45 with client browsers 50 to provide access to the cognitive computing system for one or more users; and data sources 10, 20. The computer server system 25, client systems 45 and data sources 10, 20 may be remote from each other and communicate over a network 40. The cognitive computing system 30 is a specialized system, while the client browsers 50 are implemented by any conventional or other web browser that can be connected to the internet and configured to access the cognitive computing system.

The data source 10 may be one or more structured data sources, while data source 20 may be one or more unstructured data sources. The structured data sources could be related to past clinical research study performance (e.g., compliance, speed, start-up, enrollment, violations, audit outcomes, etc.) and/or to an investigator, provider, and research site characteristics and patient population. A description of possible structured data sources is discussed in more detail below. The unstructured data sources could be medical journals, publications, web pages, and/or any relevant real-world information that is in a natural language (i.e., a language that has developed naturally in use, as contrasted with an artificial language or computer code) and can be accessed in a textual form.

The cognitive computing system 30 is a computational approach to augment human intelligence. Four main characteristics exhibited by this class of system are understand, reason, interact, and learn. For embodiments of the present invention, the underlying software understands the clinical research performance and/or therapeutic area and the specific research study eligibility criteria in question, reasons over relevant data made available, interacts by presenting the ranked investigators to the user, and learns from feedback provided by the user.

The network 40 is the connection between the user and server 25 housing the cognitive computing system 30 which can communicate locally or remotely of each other and via any suitable communication medium (e.g., LAN, WAN, Intranet or Internet).

The client browsers 50 enable users to query individual investigator, provider and/or research site clinical research performance data and/or generate a site optimization strategy. The browsers can also be used to submit data (e.g. compliance, speed, start-up, enrollment, violations, audit outcomes, etc.) to cognitive computing system 30 which can be used to determine a performance score, rank and match. The browsers 50 may present a graphical user (e.g., GUI, etc.) or other interface (e.g., command line prompts, menu screens, etc.) to solicit information from users pertaining to the desired metrics and analysis, and may provide reports including analysis results (e.g., performance scores, etc.), ranking results, and site optimization plan.

Server system 25 and client systems 45 may be implemented by any conventional or other computer systems preferably equipped with a display or monitor, a base (e.g., including at least one processor 2, one or more memories 6 and/or internal or external network interfaces or communications devices 4 (e.g., modem, network cards, etc.)), optional input devices (e.g., a keyboard, mouse or other input device), and any commercially available and custom software (e.g., server/communications software, cognitive computing system, browser/interface software, etc.).

As further shown in FIG. 1, the cognitive computing system 30 may include a structured data acquisition module 55 that can be connected to the one or more structured data sources 10 on demand or scheduled to do an Extract, Transform, and Load (ETL) of the available data; a content acquisition module 60 that is similar to the structured data acquisition module 55 except it ingests vast amounts of unstructured data from one or more unstructured data sources 20, e.g., journal articles, past study results, clinical protocols, etc.; and a natural language processor (NLP) 65 which parses unstructured content, for example, literature authored by an investigator to determine how relevant the literature is for the given research study being analyzed in order to set a score and/or rank for the investigator. The natural language processor can also read other unstructured content, such as prior clinical research studies, journals, websites, etc., in order to mine for data to use in establishing a ranking of the investigator.

Techniques used in the natural language processor (NLP) 65 for information extraction may include: (a) interpreting the overall document structure and breaking the document down into paragraphs and sentences; (b) parsing text and finding any mention of biomedical concepts (e.g., genes and proteins) in the text; (c) interpreting the relationships between those concepts expressed in the text; (d) co-references that determine implied meaning between sentences or paragraphs (e.g., "Drug xyz is effective for abc. It has been proven with evidence . . . " the reference of "It" is co-referenced with Drug xyz); (e) parsing sentences by a parser to understand the syntax of each sentence; (f) tokenizing each sentence into individual words or tokens to determine the parts of speech (POS) for each word in a sentence (e.g., noun, verb, preposition, adjective, etc.); (g) syntactic organization to determine the syntactic organization of a sentence (e.g., subject, verb, object, clauses, and phrases); (h) semantic variations, (e.g., determining if "HTN" or "Hypertension" are semantically the same); and (i) context association which is determining the sense or meaning of each token based on the context (e.g., Hypertension in a patient's family history is different from Hypertension in a patient's own medical history).

Additionally, the cognitive computing system 30 includes a data aggregator module 70 that is used to aggregate known information about the investigator, provider or research site, including structured data from the structured data acquisition module 55 and features extracted from unstructured data through natural language processor (NLP) 65, in order to compile raw data of relevant metrics for a given research study that will be subsequently used by analytical modules. For example, patient population data may be aggregated by demographic characteristics, diagnosis codes, lab results, medication utilization, or other data points necessary to analyze clinical research eligibility criteria. Further, the data aggregator module 70 aggregates the features extracted from NLP 65 to ultimately feed a knowledge store 90.

Data aggregation provides a single source of truth across all known data (structured and unstructured) about a particular research study. While building knowledge in a particular therapeutic area, the process of data aggregation may be repeated over several studies to get the knowledge store fully populated for that particular therapeutic area. For example, if breast cancer is the therapeutic area, all known clinical attributes about breast cancer, including tumor staging, bio-marker, and general characteristics of breast cancer, are aggregated as an ontology to assist the analytical modules and the building of the knowledge store 90.

As previously mentioned, the data aggregator 70 aggregates the features extracted from NLP 65 and feeds the features to knowledge store 90 of cognitive computing system 30 (see FIG. 1). The knowledge store 90 creates an ontology structure which includes various entities and relationships that will be required by a site optimizer 95 (FIG. 1), as discussed in more detail below. For embodiments of the present invention, the ontology created by the knowledge store 90 may be made up of a literature content hierarchy. For example, the literature content hierarchy may include (a) therapeutic area, (b) investigator/author list, and (c) other pertinent parameters, such as number of published articles, reviews, relevance, date of publication, journal type, rating of articles, speaker engagements, survey results, etc. However, it is contemplated that one or more other pertinent parameters can be added at a later point if necessary or desired. In addition, the ontology may also include clinical research parameters of the given study, patient population characteristics, and past clinical research parameters.

Referring again to FIG. 1, the cognitive computing system 30 includes machine learning (ML) model 75 that encompasses methods of learning from examples and reveals hidden structure in data. A supervised machine learning (SML) model learns from examples, and a model is trained to provide an estimate of the output using training data available from past clinical research performance as well as other available data. The model is initially trained on past performance data and will continuously learn through data over time. Further, the cognitive computing system 30 may interact with the user in order to extract feedback on the investigator ranking and site optimization plan to re-train the machine learning model.

In embodiments of the present invention, two types of machine learning techniques may be used to train or re-train the machine learning model.

To train or re-train the machine learning model for an investigator score, rank and/or match, the data aggregated may be processed using a linear regression model, such as Lasso or Ridge regression, since there is collinearity in the data points as well as other important features in the data. The input to this model is a feature vector based on therapeutic area(s) and domains described in more detail below. The output of this model is an outcome variable that contains the investigator's score, rank and/or match.

To train or re-train the machine learning model for site optimization (using site optimizer 95), the data aggregated may be processed using a K-Means clustering model. However, it is contemplated that other ML models, such as CART (Classification and Regression Trees), which is a type of decision tree, may be used to account for variations in data across studies and therapeutic areas. The input to this model is a feature vector based on therapeutic area(s) and domains described in more detail before. The output of this model is an outcome variable that contains the site, rank and/or match.

Referring to FIG. 1 again, the cognitive computing system shown in FIG. 1 includes a score and rank module 80 that is used to analyze individual investigator, provider and/or research site clinical performance data, calculate the performance score, as described below, and rank them on the relevance to the given clinical research. The performance score is configured to be an objective, highly accurate numerical evaluation based on the individual investigator, referred to as the investigator performance score, and/or site clinical research performance history, referred to as the site performance score. The performance score is expected to be available across the clinical research industry as a performance score very similar to a credit rating score and will provide investigators with an accompanying performance report to drive behavior change.

Further, the cognitive computing system shown in FIG. 1 includes a predictive model 85 that can be used to make predictions with new data using previously trained machine learning (ML) models. For example, the score of an investigator or the score of a research site may be generated from the ML models and the incoming new data from the data aggregator 70 after it is scored and ranked in the score and rank module 80. The predictive model 85 is similar to machine learning (ML) model 75 and may be any one of a linear regression model, such as Lasso or Ridge regression, a K-Means clustering model, and a CART (Classification and Regression Trees) model, as discussed above. Deterministic rules can be built into the predictive model for performance areas which do not have historical data points. The input to predictive model 85 is a feature vector based on therapeutic areas(s) and domains described in more detail below. The output of the predictive model is a contour graph of all the ranked sites and investigators for that particular research study.

The score and rank module 80 initially uses the weighted combination of metrics to compute performance/site scores. These scores are used to train machine learning (ML) model 75 to compute performance scores, rank and/or match. The performance scores are normalized and ranked by score and rank module 80. Once machine learning (ML) model 75 is trained, site optimizer 95 will obtain data (factors) requests from users and provide data (factors) to predictive model 85. The predictive model uses the performance scores computed by machine learning (ML) model 75, new structured/unstructured data pertaining to the data, and the data (factors) requests to determine (calculate) the rank and match of investigators/sites.

In addition, the cognitive computing system 30 includes a site optimizer 95 that is used to interact with the users to optimize the research sites that can provide the necessary patients given the investigator scores in those sites as well as the patient population that matches the eligibility criteria of the given study. This optimizer component interacts with knowledge store 90 to perform this function. There may be some cases where site optimizer 95 triggers the underlying predictive model 85, as well as the score and rank module 80, to re-run in case of a change in the optimization goal. For example, if users want to optimize by timeline, more sites will be needed to come up with the required number of patients. On the other hand, if the optimization is by cost, lesser sites but more time will be required to recruit the patients.

According to certain embodiments thereof, the performance score creates an industry-wide approach for shared clinical research success. Specifically, the performance score will provide industry, foundations, private donors, academic medical centers, government sponsors, etc., with a verifiable, objective, easy, and independent way to identify appropriate investigator performance history, which should reduce investment risk and increase chances for meeting enrollment targets and contract/agreement expectations. The impact of the performance score on investigators will be an increased transparency into their research performance history since a "score card" of their performance will be readily available industry-wide. Also, sharing data on investigators with certain scores, indications, experience, and geographical location will expedite study placement/site selection. Additionally, Academic Medical Centers (AMC) may use the performance score to decide continued funding allocations for investigator-initiated projects. Clinical research sponsors could use the system to generate ranked lists of investigators based on their score and a site optimization plan that is study specific, as shown, for example, in FIGS. 3-5.

As discussed above, the performance score is an objective, highly accurate numerical evaluation based on the individual investigator's clinical research performance history that can be used to decrease the risk of a Sponsor's investment in a site as it provides greater transparency into an individual investigator's clinical research performance. The approach involves gathering individual investigator clinical research performance data across studies (such as compliance, speed, start-up, enrollment, violations, audit outcomes, etc.) and making this data available industry-wide as a performance score similar to a credit rating. However, unlike the typical credit rating approach, this approach will provide investigators with an accompanying report to drive behavior change.

The accompanying report referred to above may include: 1) connections for service/technology providers to improve sub-par scores (when applicable), and 2) the ability to provide feedback about the sponsors and clinical research organizations (CROs) with which they are engaged. However, it should be appreciated that any other suitable and meaningful information that would be helpful to drive behavior change could be included in the report. Further, the information for producing the performance score may be obtained by the web-based computer-implemented system (running software applications) from various data sources (e.g., registries, data for purchase, etc.), preferably over a network.

The initial performance score of an individual investigator is preferably a weighted score and may be determined (calculated) in score and rank module 80 based on one or more metrics associated with clinical research performance. For example, the performance score may be calculated based on metrics from the following domains (performance areas): (a) Compliance History; (b) Ethical Conduct History; (c) Study History Length; (d) Enrollment Study History; (e) Enrollment Study-Wide; (f) Study Mix; (g) Engagement Study-Wide; and (h) Standards One; (i) Standards Two; and (j) Investigator Background and Expertise.

Furthermore, natural language processing and machine learning models are used on top of the performance score to rank and match entities using additional structured and unstructured data. If for example, the disease area is breast cancer, then all known investigators are retrieved from the data aggregator with investigators who have previously performed breast cancer trials along with their performance score, then ranked by the score and rank module 80. The initial performance score of investigators serves as the input to the ML model 75 when it is trained with the additional structured and unstructured data. After the ML model is trained, for a new inquiry from site optimizer 95, the predictive model then uses data from the score and rank module 80 and ML model 75 as inputs to predict the best possible investigator for that site optimizer goal. For example, if the optimization goal is to find the quickest site/investigator that can complete the study, the predictive model will get the required input from score and rank module 80 for investigators who have completed a similar study in the shortest possible time and create a contour graph using the ML model 75.

As noted above, a provider generally refers to a health care professional who helps in identifying, preventing or treating illness/disability. When a provider lacks experience conducting human subject research, the provider would not have a performance score. The provider would be included in the rank and match of potential investigators based on volume of associated patient population from medical and claims data. It is expected that once a provider gains experience in conducting human subject research, the provider would then have an investigator performance score and site performance score as data on the domains and attributes being evaluated would become available.

As further noted above, a site generally refers to the facility/entity/business under which a research study is conducted. A site performance score, for example, could include the following: a) percent of coordinators certified in clinical research at the site; b) percent of other personnel certified in clinical research at the site; c) percent of personnel who completed good clinical practice (GCP) training, i.e., completed GCP training; d) initial Institutional Review Board (IRB) approval turn-around-time; e) contract execution turn-around-time; and f) Office of Human Research Protection (or similar entity) evaluation outcome. Furthermore, natural language processing and machine learning models are used on top of the site performance score to rank and match entities using additional structured and unstructured data. If for example, the disease area is breast cancer, then all known sites are retrieved from the data aggregator with sites that have the largest population counts for breast cancer. The sites are then scored and ranked by the score and rank module 80 based on the parameters above. This ranked list of sites serves as the input to the ML model 75 when it is trained with the data. After the ML model is trained, for a new inquiry from site optimizer 95, the predictive model then uses data from the score and rank module 80 and ML model 75 as inputs to predict the best possible site for that site optimizer goal. For example, if the optimization goal is to find the least expensive site that can complete the study, the predictive model 85 will get the required input from score and rank module 80 for sites who have completed a similar study with low costs and create a contour graph using the ML model 75.

Within each domain (performance area) metric, data representing a characteristic of the performance area with one or more attributes (performance conditions for the characteristic) are provided. Point values are given to each domain attribute and a weight value is assigned to the domain characteristic. The performance scores (for investigators and sites) are based on a summation of the weighted points from one or more of these domains, as described in detail below. The investigator performance score may be used alone or in combination with a site performance score or providers within the same organization.

For the Compliance History domain, (a) the characteristic to be addressed may be compliance issues and number of months since the most recent compliance issue and (b) the attributes to be addressed may be one or more of: (i) no public records; (ii) study closed due to compliance issue(s) by principal investigator/research team; (iii) Food and Drug Administration (FDA) inspected and no action indicated (NAI); (iv) Food and Drug Administration (FDA) inspected and voluntary action indicated (VAI); (v) studies closed early due to lack of performance by principal investigator (PI); (vi) Food and Drug Administration (FDA) inspected and official action indicated (also known as FDA Form 483, Inspection Observations; and (vii) barred from research/debarred. The weighted points for these characteristic/attributes are used to provide (calculate) the domain score for this domain. It is contemplated, however, that any other suitable characteristic/attributes may be included for consideration within this domain.

For the Ethical Conduct History domain, (a) the characteristic to be addressed may be type of issue and number of months since the most recent compliance issue and (b) the attributes to be addressed may be one or more of: (i) research conducted without prior Institutional Review Board (IRB) approval; (ii) minor reporting/violation issues; (iii) no reported issues; (iv) failed Institutional Review Board (IRB) timely reporting; (v) reported to Office of Human Research Protections (OHRP) due to significant non-compliance; (vi) reported to Office of Human Research Protections (OHRP) due to continuing non-compliance; and (vii) termination by Institutional Review Board (IRB) due to non-compliance. The weighted points for these characteristic/attributes are used to provide (calculate) the domain score for this domain. However, it is contemplated that any other suitable characteristic/attributes may be included for consideration within this domain.

For the Study History domain, (a) the characteristic to be addressed may be number of studies associated with the investigator, provider or research site and (b) the attributes to be addressed may be one or more of: (i) equal to or below three studies; (ii) four to ten studies; and (iii) eleven to seventeen studies. The weighted points for these characteristic/attributes are used to provide (calculate) the domain score for this domain. It is further contemplated, however, that any other suitable characteristic/attributes may be included for consideration within this domain as well.

For the Enrollment Study History domain, (a) the characteristic to be addressed may be average enrollment history associated with the investigator or research site and (b) the attributes to be addressed may be one or more of: (i) enrolled 70% of site target or better; (ii) enrolled 60% of site target; (iii) enrolled 50% of site target; (iv) enrolled 40% of site target; (v) enrolled 30% of site target; (vi) enrolled 20% of site target; and (vii) enrolled 10% of site target. Again, the weighted points for these characteristic/attributes are used to provide (calculate) the domain score for this domain. Also, it is contemplated that any other suitable characteristic/attributes may be included for consideration within this domain.

For the Enrollment Study-Wide domain, (a) the characteristic to be addressed may be median enrollment history across sites, regions, etc. and (b) the attributes to be addressed may be one or more of: (i) top 20% enrollment; (ii) top 30% enrollment; (iii) top 40% enrollment; (iv) 50%-70% enrollment; (v) lowest 20% enrollment; and (vi) lowest 10% enrollment. The weighted points for these characteristic/attributes are used to provide (calculate) the domain score for this domain. Further, it is contemplated that any other suitable characteristic/attributes may be included for consideration within this domain.

For the Study Mix domain, (a) the characteristic to be addressed may be investigator, provider or research site experience with different study types/phases/specialties and (b) the attributes to be addressed may be one or more of: (i) non-clinical trial; (ii) phase two and/or phase three; (iii) phase one; and (iv) phase. Again, the weighted points for these characteristic/attributes are used to provide (calculate) the domain score for this domain. It is contemplated, however, that any other suitable characteristic/attributes may also be included for consideration within this domain.

For the Engagement Study-Wide domain, (a) the characteristic to be addressed may be average speed to start and (b) the attributes to be addressed may be one or more of: (i) over 120 days to initiation/approval/first enrollment; (ii) 90 to 120 days to initiation/approval/first enrollment; (iii) 76 to 90 days to initiation/approval/first enrollment; (iv) 61 to 75 days to initiation/approval/first enrollment; (v) 46 to 60 days to initiation/approval/first enrollment; (vi) 31 to 45 days to initiation/approval/first enrollment; (vii) 30 days or less to initiation/approval/first enrollment; and (viii) no enrollment. The weighted points for these characteristic/attributes are used to provide (calculate) the domain score for this domain. However, as mentioned before, it is contemplated that any other suitable characteristic/attributes may be included for consideration within this domain.

For the Standards One domain, (a) the characteristic to be addressed may be certification in Human Subjects Review (HSR), Good Clinical Practice (GCP), etc. and (b) the attributes to be addressed may be at least: Principal Investigator (PI) is certified. Again, the weighted points for this characteristic/attribute is used to provide (calculate) the domain score for this domain. However, it is contemplated that any other suitable characteristic/attribute may be included for consideration within this domain.

For the Standards Two domain, (a) the characteristic to be addressed may be Begin with certification in Human Subjects Review (HSR), Good Clinical Practice (GCP), etc. and (b) the attributes to be addressed may be at least: coordinator (COORD) is certified. Again, the weighted points for this characteristic/attribute is used to provide (calculate) the domain score for this domain. Moreover, as previously mentioned, it is contemplated that any other suitable characteristic/attribute may be included for consideration within this domain.

For the Investigator Background and Expertise domain, (a) the characteristics to be addressed may be publications, speaking engagements, professional organization committee participation, and social media and (b) the attributes to be addressed may be one or more of: (i) number of publications and speaking engagements; (ii) impact scores of journals where published; (iii) author position (e.g., lead author, last author, etc.); (iv) type of speaking engagements (e.g., keynote, conference presentation, continuing medical education module, etc.); (v) type of committee participation (e.g., regulatory, research, guideline formation, etc.); (vi) committee position (e.g., chair or member); and (vii) size of social network. The weighted points for these characteristic/attributes are used to provide (calculate) the domain score for this domain. However, it is contemplated that other suitable characteristic/attributes may be included for consideration within this domain on a study-specific basis, such as specialty training and experience performing study-specific procedures.

Once the characteristic/attributes of one or more of the domains have been addressed, and time element factored for applicable characteristic/attributes, the appropriate points (P) associated with the characteristic/attributes of one or more domains are multiplied by the assigned weight factor (W) to provide a domain score (W×P) for the domain. Thereafter, the domain scores for one or more of the domains are summed (combined) to produce a performance score for a particular study, as well as to produce a performance score for the individual investigator and/or the research site indicating a degree of clinical research performance. Moreover, the individual investigator may be provided with information on what to do to improve his/her score. Also, the performance score may be normalized or compared based on various criteria, such as a value range for the performance score, performance scores of individuals within a geographical region and scores for particular quantities of clinical research studies (e.g., per 100 studies, etc.).

Additionally, various searching capabilities may be employed to search based on one or more of the individual domain scores. For example, a search for investigators achieving a certain level in one or more of the domains (e.g., investigators having a domain score above a threshold for compliance issues, etc.). These searches may include Boolean or other searches to identify investigators having various combinations of the domain scores. In addition, searching based on certain domain scores or finer granularity limits data accessed and reduces processing time search to locate a desired candidate.

Furthermore, in order to provide greater insight for decision-making, the performance score may be combined with other information, such as claims data, patient population volume, etc., using natural language processing, cognitive learning models to match and rank for a given research study.

Figure 2:
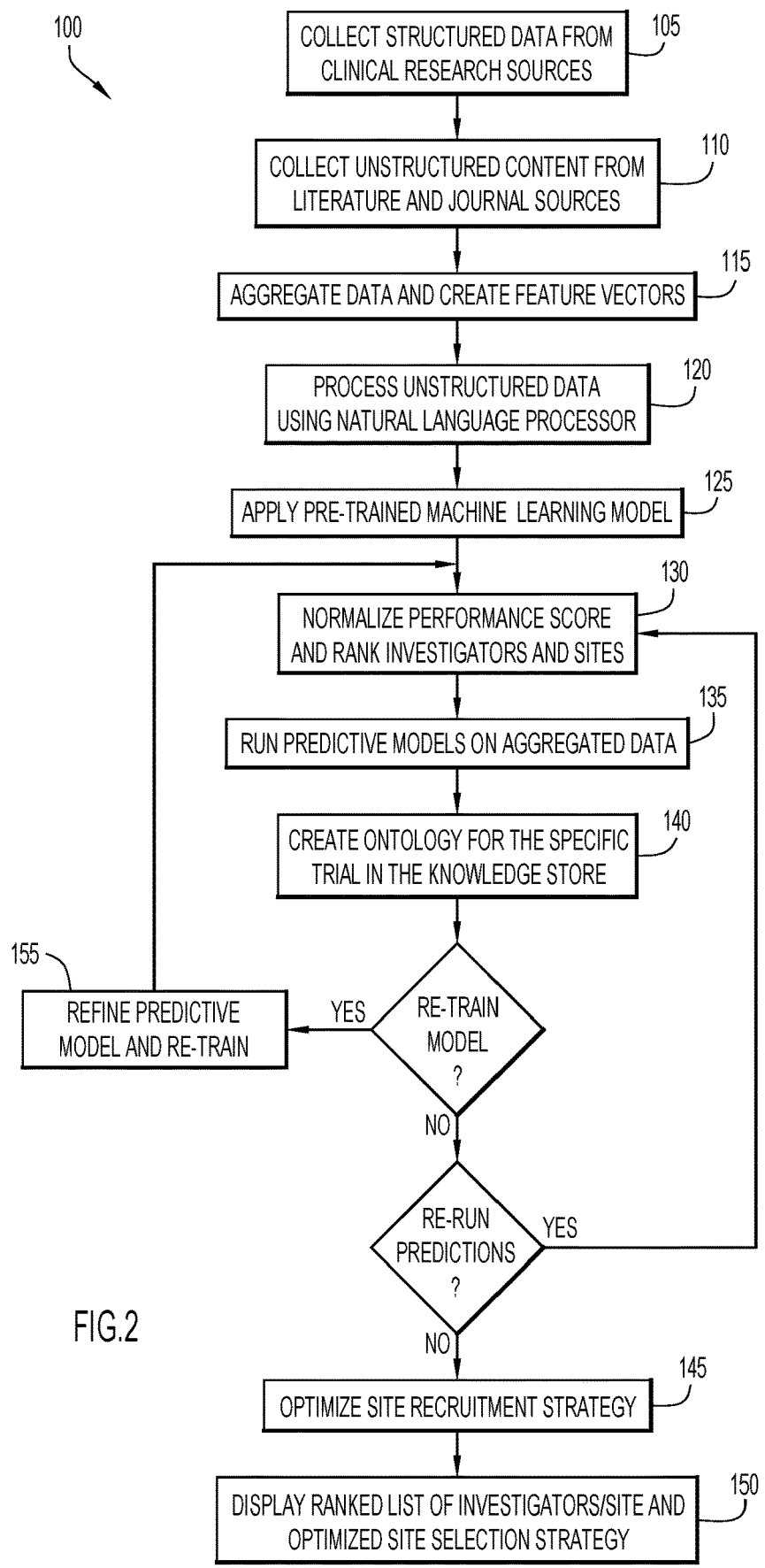
FIG. 2 presents a flowchart of an example computer-implemented method for determining an entity's clinical research performance score and rank along with the site optimization strategy (match based on protocol eligibility criteria) in accordance with various aspects and embodiments presented herein.

Referring to FIG. 2, shown is an example flowchart 100 of an exemplary computer-implemented method for determining investigator, provider and site clinical research performance scores in accordance with aspects of certain embodiments presented herein. The method begins at step 105 where data acquisition module 55 of cognitive computing system 30 collects structured data from one or more clinical research sources 10. Upon collecting the structured data, the cognitive computing system further collects unstructured content from one or more literature and journal sources 20 via content acquisition module 60 at step 110.

At step 115, structured data acquired by data acquisition module 55 are aggregated by data aggregator 70 and feature vectors are created. At step 120, the unstructured data acquired by content acquisition module 60 are processed by natural language processor 65. Once processed, the data are aggregated by data aggregator 70 and feature vectors are created.

At step 125, machine learning (ML) model 75 (trained as described above) is applied to the aggregated data and a performance score and rank for investigators and sites is calculated. At step 130, the score and rank module 80 normalizes the calculated performance score and rank for investigators and sites. Normalization helps take into account the sparsity of the data points. Module 80 computes the initial score for site and investigator using appropriate parameters and weighted scores for the calculation as described above. For example, an investigator score could be based on parameters from the compliance history domain whereas a site score can be based on the number of investigators who are GCP certified.

At step 135, predictive models are run on the aggregated data. Thereafter, ontology for the specific trial is created in the knowledge store 90 (step 140). Next, a determination is made as to whether the predictive model 85 needs to be re-trained, based on the site optimizer goal (e.g., if the predictive model picked an incorrect site based on the user judgment for an optimization goal, the user can force the re-training of the model from the user interface). If yes, the predictive model is refined and re-trained (step 155). If no, a determination is made as to whether predictions should be re-run, based on a change in the optimizer goal that could result in a change in the data (e.g., if the optimization goal changes from shortest time to least cost, the data inputs to the predictive model will change as a result and the prediction should be re-run). If yes, predictions are re-run by the predictive model 85. If no, the site recruitment strategy is optimized by the triggers or factors selected from the site optimizer 95 by the user (i.e., engagement history, enrollment history, compliance history, etc.) and stored in knowledge store 90 (step 145). The triggers provided to the predictive model are used to determine the performance score and rank for a particular site.

Once the site recruitment strategy is optimized, site optimizer 95 interacts with knowledge store 90 to determine and display a ranked listing of investigator performance scores and optimized site selection strategy (step 150). The user input decides if the site selection strategy is complete and accepted by the user or if it has to be re-run by changing one or more assessment triggers depicted in FIG. 5.

Figure 3:
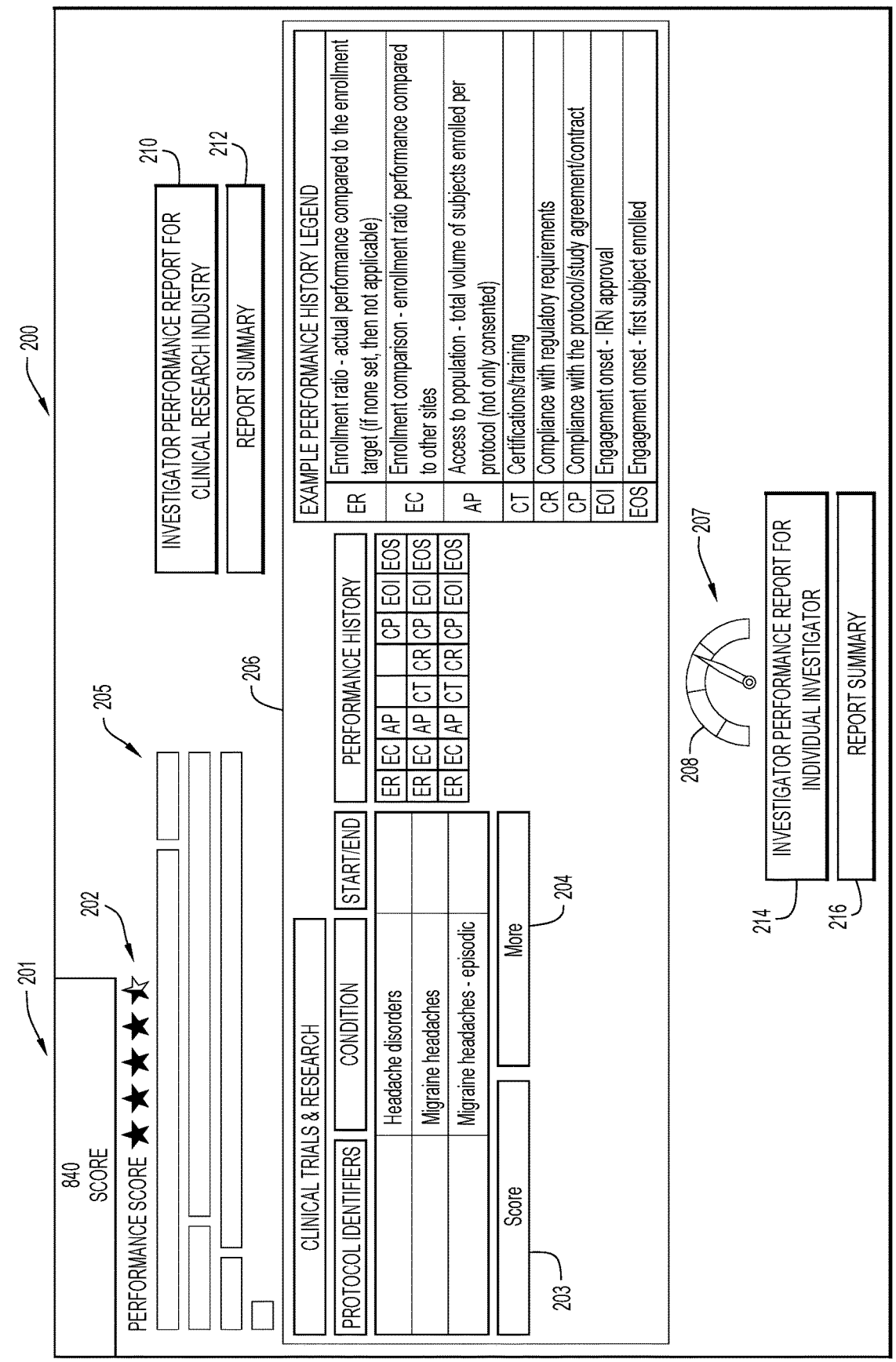
FIG. 3 is an exemplary screen shot of a graphical user interface illustrating an example performance score according to aspects of certain embodiments presented herein.

With reference now to FIG. 3, shown is an exemplary screen shot of a graphical user interface 200 illustrating an example performance score 201 according to aspects of certain embodiments presented herein. As shown, the performance score may be a three digit number designed to indicate to the clinical research industry an investigator's ability to follow-through on research study commitments. However, the performance score could further incorporate a star rating 202 as well. Based on the performance score, investigators would be referred to service/technology providers, potential study opportunities, and resources using, for example, a graphical user interface button 203. Alternatively, however, it is contemplated that individual investigators would also be able to search for the same information (e.g., service/technology providers, potential study opportunities, and resources) themselves using, for example, graphical user interface button 204. Thus, the system enables a search network to locate and connect investigators having desired characteristics with studies rather than employing a trial and error or blind approach.

Again referring to FIG. 3, the exemplary screen shot of the graphical user interface 200 may include an exemplary segmented horizontal bar chart 205 for displaying data relating to, for example, different performance areas and attributes associated with the performance score. The data in the bar graph (not shown) can be represented visually through colored sections to provide easy comparisons among performance/attribute categories. Further, the graphical user interface 200 can include a graphical representation 206 displaying data relating to research studies. The data may represent, for example, different performance areas and attributes associated with the performance areas. As shown in FIG. 3, one such performance area could include, for example, data relating to various protocols and conditions, such as (a) headache disorders; (b) migraine headaches; and (c) migraine headaches—episodic; while the attributes associated with the performance areas may include, for example, data representing (a) enrollment ratio (ER); (b) enrollment comparison (EC); (c) access to population (AP); (d) certification/training (CT); (e) compliance with regulatory requirements (CR); (f) compliance with protocol/study agreement/contract (CP); (g) engagement onset—Institutional Review Board approval (EOI); and (h) engagement onset—first subject enrolled (EOS). The displayed data may be depicted as a bar graph with the data represented visually through colored block-like sections to provide easy comparisons among performance/attribute categories. Each block-like section may also have an abbreviation superimposed thereon relating to one of the performance/attribute categories set forth above.

Further, the graphical user interface 200 shown in the FIG. 3 embodiment of the present invention may include an exemplary simple radial dial chart 207. As illustrated, the radial dial chart may comprise various geometric-shaped segments 208 creating qualitative ranges to classify an individual investigator's performance. These ranges enable users of the computer-implemented monitoring system to quickly monitor, visualize, and measure the progress of an individual investigator toward a specific goal, for example, an investigator's ability to follow-through on research study commitments.

Each geometric-shaped segment 208 of the radial dial chart 207 could have a different background color, border color, word designation, etc. to differentiate them from one another. For example, the geometric-shaped segments could have four color ranges marked red, orange, green, and gold, each having its own unique range value. At a glance, the "red" color segment would indicate to a user "poor" investigator performance; the "orange" color would indicate "fair" investigator performance; the "green" color would indicate "good" investigator performance; and the "gold" color would indicate "excellent" investigator performance. Moreover, it is contemplated that the background of the radial dial chart may be composed of one or more different colors, if desired.

Again referring to FIG. 3, the example graphical user interface 200 may include an investigator performance report 210 providing a comprehensive description of the performance score, as well as an investigator performance summary report 212 summarizing key aspects of the performance report 210. Each report can be used by the clinical research industry to assist with the selection of best matched candidates (i.e., individual investigators, providers, and/or research sites) to participate in clinical research studies, e.g., clinical research trials, or for any other desired purpose. Further, the example graphical user interface 200 can include an investigator performance report 214 having information that may be used by an individual investigator to drive behavioral change, and an investigator summary report 216 that typically may contain recommendations to elicit and/or encourage investigator behavior change.

Figure 4:
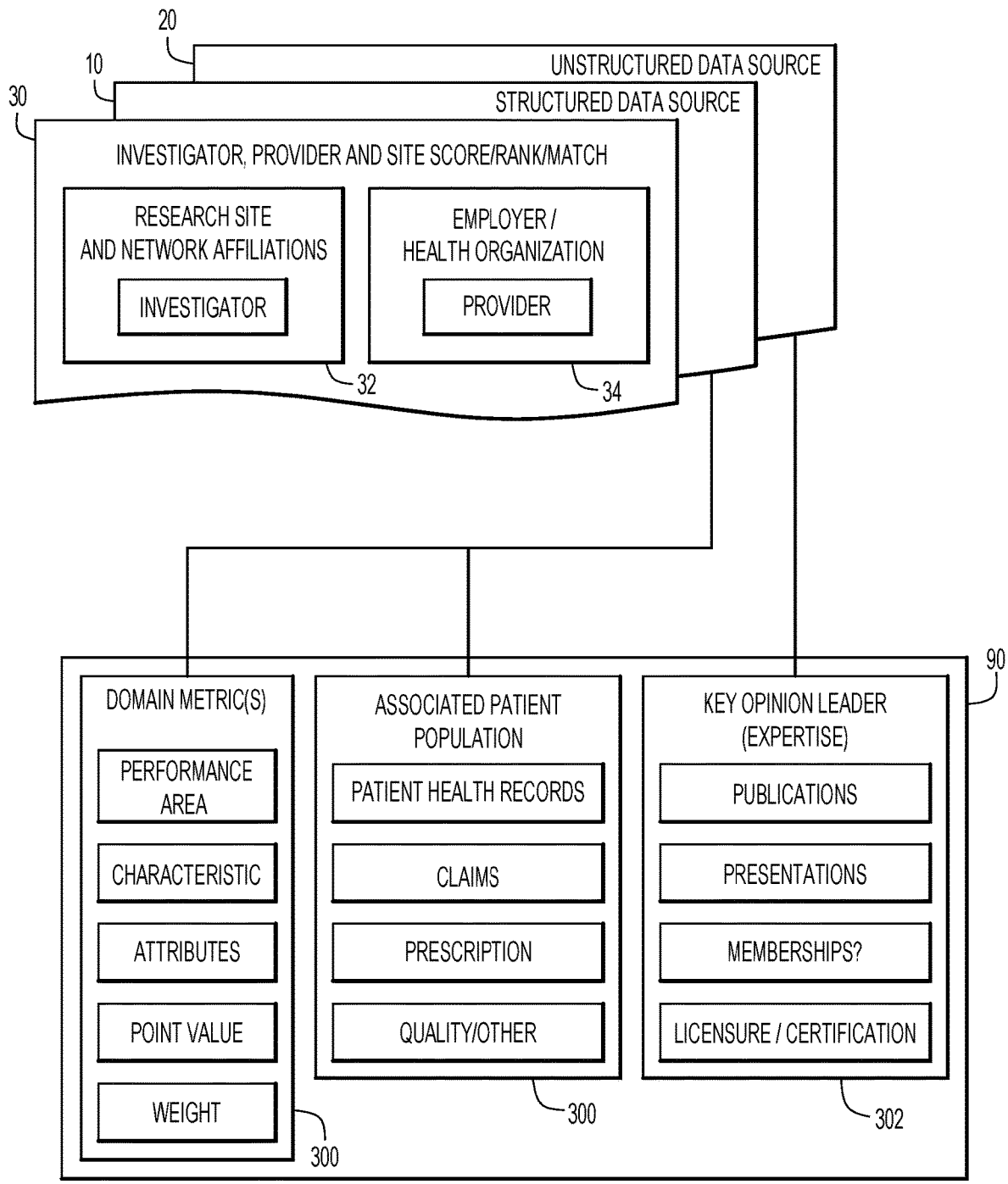
FIG. 4 is a high level depiction of example data used to create one or more entities' (e.g., investigator, provider, research site, etc.) performance score, rank and match in accordance with various aspects and embodiments presented herein.

Referring now to FIG. 4, shown is a high level depiction of example data 300 (e.g., domain metrics data, associated patient population data, etc.) acquired by structured data acquisition module 55 of cognitive computing system 30 (FIG. 1) from structured data sources 10, aggregated by data aggregator 70, and stored in knowledge store 90 that can be used to create the performance score, rank and match of one or more entities (e.g., investigator, provider, research site, etc.) in accordance with certain embodiments presented herein. Further shown is a high-level depiction of example data (key opinion leader (expertise) data, etc.) 302 acquired by content acquisition module 60 of cognitive computing system 30 (FIG. 1) from unstructured data sources 20, parsed by natural language processor (NLP) 65, aggregated by data aggregator 70, and stored in knowledge store 90 that can be also used to create the performance score, rank and match of one or more entities (e.g., investigator, provider, research site, etc.) in accordance with certain embodiments presented herein. Additionally, the box 32, shown within cognitive computing system 30, represents the data for the investigator. Similarly, the box 34, shown within cognitive computing system 30, represents the data for the provider score.

Figure 5:
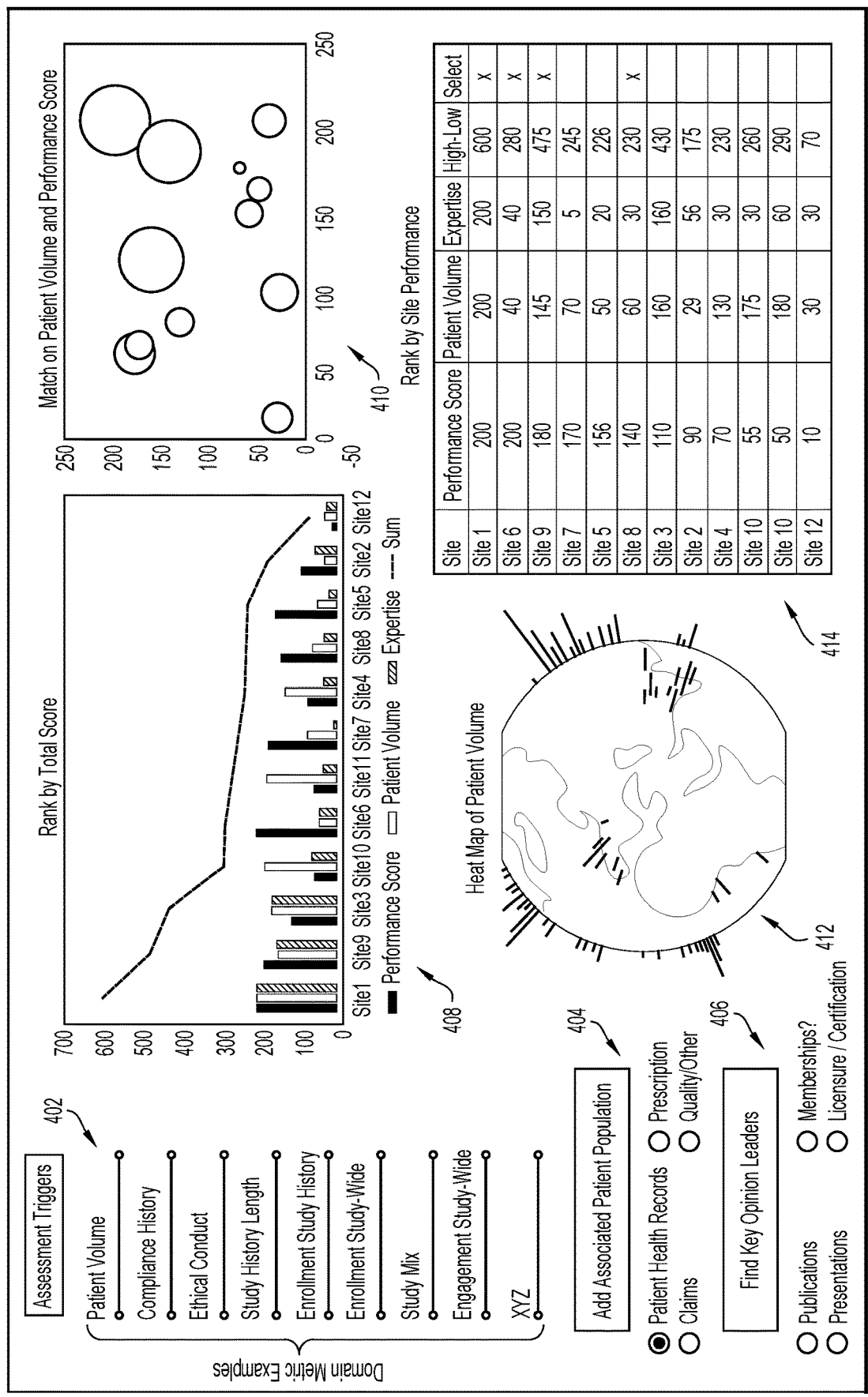
FIG. 5 is an exemplary screen shot of a graphical user interface illustrating an example result of running a query to determine one or more entities (e.g., investigator, provider, and research site, etc.) with the best matched performance score and rank according to protocol-specific eligibility criteria in accordance with various aspects and embodiments presented herein.

FIG. 5 presents an exemplary screen shot of a graphical user interface 400 illustrating an example result of running a query to determine one or more entities (e.g., investigator, provider, research site, etc.) with best matched performance score and rank according to protocol-specific eligibility criteria in accordance with certain aspects and embodiments presented herein. As may be seen in FIG. 5, the example result shown on user interface 400 may depict at least the following information: (a) one or more assessment triggers 402 based on domain (performance area) metrics discussed previously; (b) associated patient population data 404 pulled in, for example, from (i) patient population health records, (ii) claims, (iii) prescriptions, and (iv) quality/other; and (c) key opinion leaders (experts) data 406 pulled in, for example, from (i) publications, (ii) presentations, (iii) memberships, and (iv) licensure/certification. Moreover, the best matched performance score and rank according to protocol-specific eligibility criteria may be shown on user interface 400 using one or more graphical representations 408-414.

Again referring to FIG. 5, the protocol-specific eligibility criteria employed to determine best matched performance score and rank for one or more the entities (investigator, provider, and/or site) may be graphically displayed using different charts and graphs. In FIG. 5, the following example charts/graphs are used to depict best matched performance score and rank for one or more of the entities (investigator, provider and/or site):

(1) A classic column-based bar graph or chart (not shown) or a combination column-based/line-based graph or chart 408 which ranks sites, for example, by total score. One axis of this graph may feature site categories to be compared, while the other axis could represent the score of the site category. With one quick glance, users can learn exactly how the various sites size up against one another.

(2) A bubble graph or chart 410 which ranks sites, for example, based on matched patient population volume and performance score. This type of graph compares the relationships between data objects in 3 numeric-data dimensions: X-axis data, Y-axis data, and data represented by the bubble size.

(3) A static or interactive heat map graph or chart 412 which ranks sites, for example, based on patient population volume. The graphical representation of data in this type of graph is displayed as colors or length of line instead of numbers, and provides an immediate visual summary of information.

(4) A treemap graph or chart 414 which ranks sites, for example, based by site performance. This type of graph provides a quick, high level summary of similarities and anomalies within one category, as well as between multiple categories, for a large number clinical research sites at the same time.

To summarize aspects of certain example embodiments of the present invention presented herein:
(1) The performance score enables users to:
  Create ways to select and predict which investigators and research sites would perform well for a given research study.
  Use Real World Evidence (RWE) to optimize strong protocols and matching sites based on population and performance—a vital behavior to streamline the execution of studies.
  Indicate best site/principal investigator (PI) match for studies during site selection and planning of a research study, based on site and investigator performance scores.
  Use performance scoring to inform and improve clinical research operations at the site level and at contract research organizations (CRO)/sponsor companies.

Connect users to resources necessary to improve performance (e.g., process improvement and Business-To-Business improvement).

Aggregate multiple sources of data that could influence/predict performance.

Provide cognitive match between clinical research protocols and investigators/sites.

(2) Example data types useable to produce the performance score are:

Study-specific performance history (inclusive of operational metrics, ethical, quality, compliance performance history, resources, certifications, laboratory, claims, prescriptions, health, publications, facility costs, aggregate patient population, study conduct history, training, key performance indicators).

Study-specific ranking/match of investigator based on investigator background and expertise (inclusive of publications and presentations).

Study-specific ranking/match and geographical representation of aggregate patient population level health data.

Investigators with clinical research participation in past, period of the study with number of patients screened and length of time to collect the data.

Providers with clinical experience and number of associated patient population.

(3) Example operational metrics usable to create the performance score are:

Key Performance Indicators (KPIs), for example, active studies, total studies, completed studies, final protocol approval to initiation/International Review Board (IRB) approval/first patient enrolled; enrollment median within study across sites, and average enrollment history.

Other critical performance, for example, ethical conduct (protocol violations) and compliance history (outcome of regulatory audits and inspections).

Matches, for example, those based on study experience, standards, volume of patient population that match eligibility criteria (laboratory results, prescription, claims, medical records, costs), etc.

By gathering data centrally, users may observe site and investigator performance in aggregate form.

It will be appreciated that the embodiments described above and illustrated in the drawings represent only a few of the many ways of implementing embodiments for monitoring clinical research performance.

The environment of the present invention embodiments may include any number of computer or other processing systems (e.g., client or user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, cognitive computing system, etc.). These systems may include any types of monitors and input devices (e.g., keyboard, mouse, voice recognition, etc.) to enter and/or view information.

It is to be understood that the software (e.g., cognitive computing system) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., cognitive computing system) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to the server and/or client systems. The database systems and/or storage structures may be remote from or local to the computer or other processing systems, and may store any desired data.

The present invention embodiments may employ any number of any type of user interface (e.g., Graphical User Interface (GUI), command-line, prompt, etc.) for obtaining or providing information (e.g., query statements), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The charts 205, 207 displayed on the graphical user interface 200 may include any information arranged in any fashion, and may be configurable based on rules or other criteria to provide desired information to a user.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention embodiments has been presented for purposes of illustration and description, but is not intended to be exhaustive or limited to the invention in the form disclosed. Many modifications and variations will be apparent to those of ordinary skill in the art without departing from the scope and spirit of the invention. The database system embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of monitoring clinical research performance comprising:
   collecting, via at least one processor, a plurality of metrics of clinical research performance for a plurality of entities across research studies, wherein each metric includes a performance area, a characteristic of the performance area with one or more attributes, point values for each attribute, and a weight value for the characteristic;
   producing, via the at least one processor, a performance score for each of the plurality of entities based on the plurality of metrics;
   generating, via the at least one processor, feature vectors based on the performance areas for the plurality of metrics, past clinical research performance, and reference medical information, wherein the feature vectors include elements corresponding to the performance areas for the plurality of metrics and the performance areas are selected from a group of compliance, ethical conduct, research study history length, enrollment history, research study wide enrollment, experience with different research studies, time to initiate a research study, certifications, and investigator background and expertise;
   training, via the at least one processor, a machine learning model with the feature vectors and the produced performance scores for the plurality of entities to determine performance scores based on the produced performance scores for the plurality of entities;
   training, via the at least one processor, a machine learning predictive model with the feature vectors and determined performance scores from the machine learning model to determine corresponding entities for conducting clinical research;
   processing a request for entities, via the at least one processor, by applying the performance scores for the entities of the request from the machine learning model and feature vectors generated from appropriate corresponding data for the entities of the request from the performance areas for the plurality of metrics, past clinical research performance, and reference medical information to the machine learning predictive model to determine resulting performance scores for the plurality of entities and corresponding entities to conduct the clinical research;
   performing, via the at least one processor, entity assessment actions based on the resulting performance scores from the machine learning predictive model for the plurality of entities to provide clinical research performance predictions; and
   displaying, via the at least one processor, a ranked listing of the clinical research performance predictions using a graphical user interface.

2. The computer-implemented method of claim 1, wherein performing entity assessment actions comprises:
   analyzing the plurality of metrics producing the resulting performance scores for the plurality of entities and providing recommendations for the plurality of entities to improve corresponding performance scores.

3. The computer-implemented method of claim 1, further comprising:
   normalizing the produced performance scores relative to one or more from a group of a value range for the performance scores, performance scores of individuals within a geographic region, and scores for a quantity of research studies.

4. The computer-implemented method of claim 1, further comprising:
   performing a search for individuals based on performance score and one or more from a group of domain metrics, assessment triggers, and populations.

5. The computer-implemented method of claim 1, wherein performing entity assessment actions comprises:
   referring an individual to service providers for research studies based on a corresponding resulting performance score.

* * * * *